United States Patent [19]

Wurtman et al.

[11] Patent Number: 4,470,987
[45] Date of Patent: Sep. 11, 1984

[54] PROCESS FOR TREATMENT AND PREVENTION OF VENTRICULAR FIBRILLATION

[75] Inventors: Richard J. Wurtman, Boston; Bernard Lown, Chestnut Hill, both of Mass.

[73] Assignee: Massachusetts Institute of Technology, Cambridge, Mass.

[21] Appl. No.: 264,522

[22] Filed: May 18, 1981

Related U.S. Application Data

[62] Division of Ser. No. 122,422, Feb. 19, 1980, Pat. No. 4,271,192.

[51] Int. Cl.³ ............... A61K 31/49; A61K 31/44; A61K 31/135; A61K 31/195
[52] U.S. Cl. ............................ 424/259; 424/263; 424/319; 424/324; 424/330
[58] Field of Search ............... 424/259, 263, 324, 330, 424/319

[56] References Cited

U.S. PATENT DOCUMENTS 3,651,237 3/1972 Laborit ........................... 424/319
4,230,719 10/1980 Kodama et al. ................. 549/79 X Primary Examiner—Richard A. Schwartz
Attorney, Agent, or Firm—Arthur A. Smith, Jr.; Paul J. Cook

[57] ABSTRACT

The risk of ventricular fibrillation in animals is reduced by administering tyrosine, a tyrosine precursor, threonine or mixtures thereof, either alone or in combination with a substance which is known to reduce the risk of ventricular fibrillation. A novel composition is provided comprising a unit dosage form of tyrosine, a precursor for tyrosine, threonine or mixtures thereof and a substance which is known to reduce the risk of ventricular fibrillation.

7 Claims, 2 Drawing Figures

PROCESS FOR TREATMENT AND PREVENTION OF VENTRICULAR FIBRILLATION

BACKGROUND OF THE INVENTION

The Government has rights in this invention pursuant to Grant No. MH-21384 awarded by the National Institute of Health to Harvard University and Grant No. AM-14228 awarded by the National Institutes of Health to the Massachusetts Institute of Technology.

This is a division of application Ser. No. 122,422 filed Feb. 19, 1980 now U.S. Pat. No. 4,271,192.

This invention relates to a method and composition for treating or preventing ventricular fibrillation in animals by increasing the levels of dopamine and norepinephrine in neuronal synapses.

It is well known that the neurotransmitters dopamine and norepinephrine are derived from dihydroxyphenylalanine (DOPA). DOPA is, in turn, produced in neurons by the enzymatic hydroxylation of the amino acid tryosine. This process is catalyzed by the enzyme tyrosine hydroxylase. The DOPA is decarboxylated to dopamine by the enzyme aromatic L-amino acid decarboxylase (AAAD) and norepinephrine is produced from dopamine in neurons that also contain the enzyme dopamine beta-hydroxylase. It is also known that within this reaction chain, the rate-limiting step is the conversion of tyrosine to DOPA. For this reason, DOPA has been administered to patients who suffer medical disability resulting from dopamine deficiency in diseases such as Parkinson's Disease. Unfortunately, DOPA, when administered, is taken up by cells throughout the body and converted to dopamine and this interferes with the normal metabolic processes in these other cells. In addition, DOPA interferes with the body's normal storage of the neurotransmitter serotonin, and lowers brain levels of the compound S-adenosylmethionine. It is believed that these effects contribute to such unwanted side effects as the "On-Off Phenomenon" and, in some patients, psychotic symptoms. Other types of drugs that act by increasing dopamine and norepinephrine levels in synapses include the Monoamine Oxidase Inhibitors (which slow the destruction of these neurotransmitters) and the tricyclic antidepressants; these compounds, which are used in treating diseases like depression are also relatively non-specific—producing many chemical effects besides increasing synaptic dopamines and norepinephrine levels—and thus have a range of unwanted side effects such as the dangerous increases in blood pressure that occur when people receiving monoamine oxidase inhibitors eat certain foods.

Ventricular fibrillation is characterized by a disorganized heartbeat induced by a multiplicity of electrical activity which does not follow the normal neuronal pathways and which appears to be caused by the presence of an excessive quantity of norepinephrine within synapses. This random electrical activity prevents synchronized contractile sequencing of the heart muscle and results in little or no blood pumping and is a common basis for sudden cardiac death. In prior art methods of treatment, patients having a substantial risk of ventricular fibrillation (V.F.) were identified by monitoring heart rhythms to determine whether extra systoles known as ventricular premature beats (V.P.B.) were present. Presently, drugs such as quinidine (6'-methoxycinchonan-9-ol) and Dilantin (5,5-diphenyl-2,4-imidazolidinedione) or procaine amide hydrochloride (4-amino-N-[2-(diethylamino)ethyl] benzamide hydrochloride) are administered to patients in order to reduce or eliminate V.P.B. While these drugs depress heart muscle function, they do not act directly on the primary cause of V.F.; namely, higher nervous activity of the central nervous system which contributes to lowering the threshold of V.F. In addition, the presently used drugs exhibit some non-specific actions as well and cause undesirable side effects including nausea, vomiting, liver impairment, thrombocytopenia, rashes and fever. Attempts also have been made to reduce the sympathetic nervous tone to the heart by administering $\beta$-adrenergic drugs. However, these drugs are nonselective in that they act on the majority of the electrical signals to the heart including those necessary for heart functioning. Furthermore, these drugs undesirably induce depression of the heart muscle and may cause weakness and impotence.

Prior attempts to increase or decrease the levels of dopamine or norepinephrine by modifying neuronal tyrosine levels had been deemed unsuccessful because the total amounts of these compounds in brains and tissues were not noted to change. It was first observed in Wurtman et al. (Science 185:183–184, July 12, 1974) that increases in brain DOPA concentrations, which, under the conditions of the experiments, varied in proportion to the rates at which dopamine and norepinephrine were being synthesized, could be obtained by increasing brain tyrosine concentrations, and that decreases in brain DOPA concentrations could be produced by giving rats treatments that decreased brain tyrosine. An example of a treatment that increased brain tyrosine was the administration of tyrosine itself; an example of a treatment that decreased brain tyrosine was the administration of one of the other neutral amino acids, e.g., leucine, that competes with tyrosine in the plasma for uptake into the brain. Prior to that disclosure, it had been believed that the rate-limiting enzyme, tyrosine hydroxylase, was so saturated with tyrosine, that increases or decreases in brain tyrosine levels would not affect tyrosine's conversion to DOPA. In neither the above Wurtman et al articles nor a subsequent paper by Gibson and Wurtman (Biochem. Pharmacology, 26:1137–1142, June, 1977) was it actually shown that such changes in DOPA accumulation were accompanied by changes in brain dopamine nor norepinephrine levels. Furthermore, in neither was it shown that changing brain tyrosine levels had any effect on the amounts of dopamine nor norepinephrine released into synapses.

It would be highly desirable to provide a means for reducing or eliminating ventricular fibrillation. Furthermore, it would be desirable to provide such a decrease with agents which do not have the undesirable effects associated with administration of procaine amide, quinidine, propranolol or the like which can cause excessive decrease in cardiac excitability. Alternatively, such agents could be used in combination with drugs now used to treat ventricular fibrillation to amplify their therapeutic effects while reducing the undesirable side effects associated with the use of these drugs.

SUMMARY OF THE INVENTION

The present invention provides a method and composition for treating or preventing ventricular fibrillation. This invention is based upon the discoveries that treatments that increase neuronal tyrosine levels can also cause corresponding increases in the amounts of norepinephrine that are released into brain synapses, and that this, in turn, diminishes the outflow of some parts of the sympathetic nervous system. The tyrosine, or a tyrosine precursor such as phenylalanine, can be administered alone or in admixtures, with or without drugs normally used to reduce ventricular fibrillation, thereby to treat or prevent ventricular fibrillation. In addition, it has been found that threonine, which does not itself affect norepinephrine levels in the brain has the effect of reducing ventricular fibrillation, perhaps by enhancing the synthesis of glycine, another neurotransmitter. Increased synaptic norepinephrine levels are obtained by giving tyrosine regardless of whether the norepinephrine-releasing neurons are or are not especially active. Phenylalanine can, in low doses, be used in place of tyrosine. The amino acids can be administered intraperitonally, subcutaneously, intramuscularly or orally; in the form of free amino acids, salts, esters, peptides or compounds which are converted to the amino acids in the body (e.g., alpha-keto acids).

DETAILED DESCRIPTION OF SPECIFIC EMBODIMENTS

Figure 1:
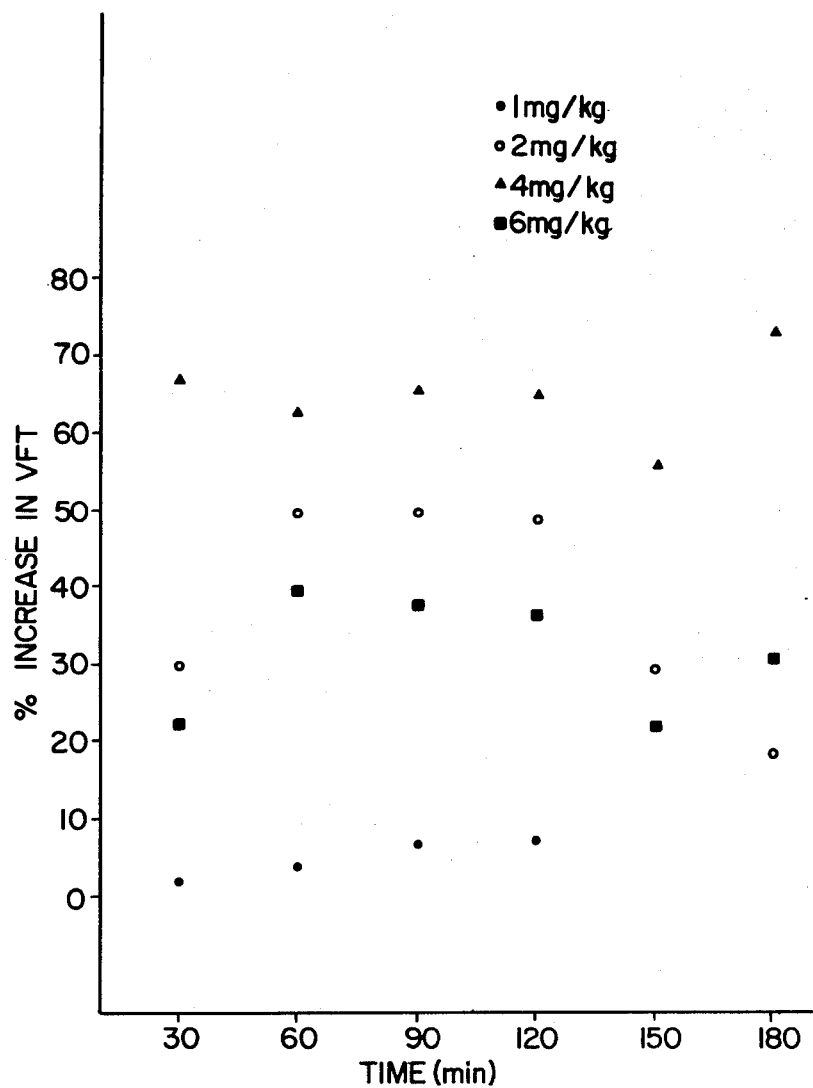

In accordance with this invention, tyrosine and/or a tyrosine precursor (such as phenylalanine) and/or threonine, is administered to a patient either alone or in combination with one or more drugs known to treat ventricular fibrillation. While the exact mechanism by which tyrosine (or threonine) reduces or prevents ventricular fibrillation has not yet been determined, it is likely that tyrosine acts by increasing the release of a catecholamine (dopamine, norepinephrine or epinephrine) into synapses, which, in turn, reduces the firing frequency of sympathetic neurons running to the heart; this decreases cardiac excitability and vulnerability.

The administration of the compositions employed in the present invention can be effected orally, intraperitonally, subcutaneously, intraveneously or intramuscularly; the amino acids can be used as such, as salts or esters, as peptides or as compounds which are metabolized to give the amino acids in vivo (e.g., Alpha-keto amino acids). Conveniently, the compositions employed in this invention are admixed or dissolved in any innocuous vehicle such as water or sterile saline solution or in tablet or powder form containing the usual solid diluents or carriers. When producing a lowering of the risk of ventricular fibrillation, the compositions employed in the present invention are administered in concentrations to avoid undesirable side effects. The compound, tyrosine, is employed in dosages sufficient to reduce the risk of ventricular fibrillation while minimizing the possibility of producing undesirable side effects such as orthostatic hypotension. In humans, useful dosages are between about 0.5 mg/kg and 250 mg/kg (depending on route of administration), preferably between about 0.5 mg/kg and 10 mg/kg when given intravenously and 10 mg/kg and 100 mg/kg when given orally. (Threonine doses are similar). Dosages below about 0.5 mg/kg body weight do not produce significant reduction of the risk of ventricular fibrillation while concentrations above about 500 mg/kg body weight do not produce significant additional lowering of the risk and may produce undesirable side effects. When utilizing this invention, reducing the risk of ventricular fibrillation is produced for about 1 to 48 hours per administration. The administration of tyrosine or phenylalanine should, if possible, be made in the absence of other amino acids that might compete for uptake in the brain and which themselves do not reduce the risk of ventricular fibrillation.

In another aspect of this invention, tyrosine, a precursor for tyrosine and/or threonine can be coadministered with drugs that are known to reduce the risk of ventricular fibrillation such as procaine amine, quinidine, propranolol, diphenylhydantoin or the like, or their pharmaceutically acceptable salts (which dissociate in vivo to produce one of these compounds) produces an additive effect of reducing the risk of ventricular fibrillation. In order to obtain this additive effect, useful concentrations of tyrosine are between about 0.5 and 50 mg/kg, preferably between about 1 and 4 mg/kg body weight (when given intravenously) together with the drug. (Larger doses are needed when given orally). In these compositions, procaine amide preferably is employed in amounts between about 28 and 42 mg/kg; quinidine in amounts between about 11 mg/kg and 23 mg/kg; propranolol in amounts between about 0.6 mg/kg and 5 mg/kg and disopyramide in amounts between about 4 mg/kg and 11 mg/kg. In some situations, phenylalanine can be used as a substitute for tyrosine in as much as this amino acid is converted to tyrosine in the liver and released into the blood stream for uptake into the brain. However, plasma phenylalanine levels should be less than about double those of tyrosine, since at the higher levels, phenylalanine competes with tyrosine for uptake into the brain, and can inhibit the enzyme tyrosine hydroxylase.

The following example illustrates the present invention and is not intended to limit the same.

EXAMPLE I

This example illustrates the desirable effect of tyrosine in increasing the threshold of ventricular fibrillation.

Healthy mongrel dogs of either sex, weighing 9–22 kg, were utilized in the present study. Anesthesia was induced with intravenous alpha chloralose (100 mg/kg; Sigma Chemical Co.; 10% wt/vol). Additional alpha chloralose, 50 mg/kg, was given when required to maintain the same level of anesthesia during the course of a study. Experiments were conducted following a lapse of at least 30 minutes after anesthetic administrations. All experiments were begun between the hours of 0830 and 0930. The animals were ventilated with a mixture of room air and 10% oxygen through a cuffed endotracheal tube using a respirator. The mixture contained approximately 40% oxygen and it maintained arterial oxygen tension between 85 and 125 mmHg. Arterial pH was maintained between 7.39 and 7.49. A polyethylene catheter was inserted into a femoral artery for sampling arterial blood and for monitoring blood pressure. A Statham P23Db transducer was employed to record systemic arterial pressure. A polyethylene catheter was also inserted into the femoral vein for anesthetic and tyrosine administration. The femoral catheter was also used to withdraw blood samples for tyrosine and catecholamine analysis.

Electrical testing of the heart was accomplished by an intracavitary lead system consisting of a transvenous bipolarpacing catheter (Medtronic, No. 5818 platinum electrodes with an interelectrode distance of 1.5 cm. and a pole width of 3 mm.) and ECG-recording probe (US Catheter and Instrument Corp., semifloating). The recording catheter was bound to the pacing catheter by silk ligatures and terminated 3.0 cm. proximal to the tip of the pacing catheter. The transvenous catheter system was wedged in the apex of the right ventricle under fluoroscopic control. Heart rate was controlled by using a variable-rate Medtronic pacemaker which delivers constant-current rectangular stimuli of 2 msec. duration. The current of the pacemaker was set at twice the diastolic threshold. The distal pole of the pacemaker was made cathodal. A testing stimulus of 5 msec. duration was employed with an electrically-isolated Grass squarewave pulse generator. A Kepco operational power supply provided constant-current stimuli (2% accuracy). The current output is directly verified by means of a Tektronix P6021 AC current probe attached to a Tektronix 6102N oscilloscope. Timing of the stimuli was controlled by using a BRS digital timer with crystal-controlled time base ($\pm 0.01$ accuracy) and equipped with appropriate circuitry to shut off the output of the pacemaker for 3.0 sec. after delivery of the test stimulus. The test impulse was delivered after every 10–15th paced beat and was synchronized from the pacer impulse.

Determination of the vulnerable period threshold for ventricular fibrillation (VF) was made in the following manner: the duration of the test stimulus was set at 5 msec. The initial current stimulus was set at 8 ma. Electrical diastole was then scanned in 5 msec. decrements beginning at the apex of the T wave and ending at the border of the refractory period. If VF is not induced with an 8 ma stimulus, the current was increased in 2 ma steps and scanning was continued until VF resulted. The lowest stimulus that elecited VF was used to define VF threshold.

VF was terminated by a DC pulse (50–150 Wsec capacitor duscharge) delivered through copper paddles (100 cm$^2$) applied securely across the thorax. This was usually accomplished within 3 sec. following the onset of the arrhythmia.

Two control VF determinations were made. Tyrosine was administered intravenously over a 20–30 min. period in dosages of 1,2,4 and 6 mg/kg. VF threshold was determined at 30, 60, 90, 120, 150 and 180 minutes after drug administration. Prior to each determination, 15 ml of blood was withdrawn from the femoral venous catheter to test for tyrosine and catecholamine levels.

Figure 2:
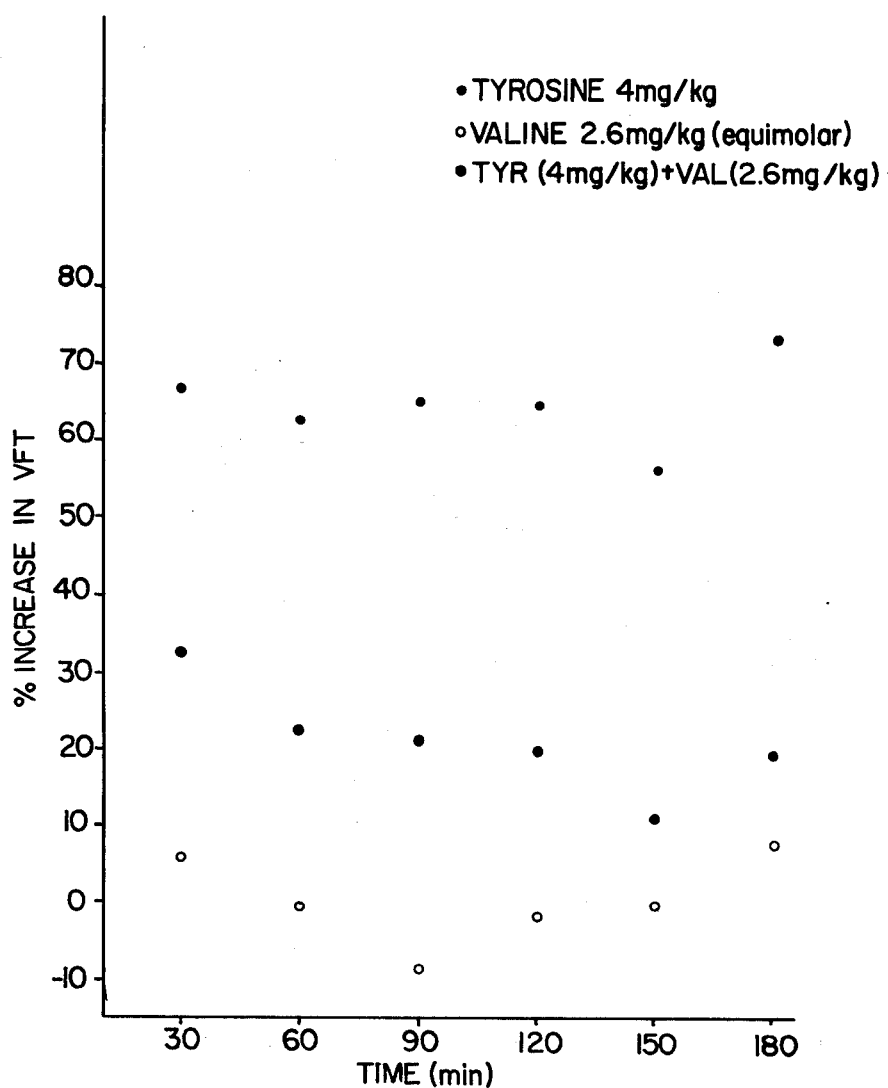

FIG. 1 shows the % increase in ventricular fibrillation threshold (VFT) as a function of time and tyrosine dosage. As shown in FIG. 1, tyrosine produced an increase in VFT even at dosages as low as 0.1 mg/kg while the desired increase in VFT was maximum at about 4 mg/kg tyrosine. As shown in FIG. 2, valine, which competes with tyrosine for uptake in the brain, reduces the desired effect of tyrosine in increasing VFT. Valine does not have an appreciable effect on VFT.

We claim:

1. The process for preventing or treating ventricular fibrillation in an animal having a condition associated with ventricular fibrillation which comprises administering to the animal a mixture of (a) a compound selected from the group consisting of tyrosine, phenylalanine, threonine or mixtures thereof and (b) a drug selected from the group consisting of procaine amide, quinidine, propranolol, disopyramide, or pharmaceutically acceptable salts thereof and mixtures thereof in an amount effective to prevent or treat ventricular fibrillation wherein the dosage of (a) is between about 0.5 and about 20 mg/kg body weight.

2. The process of claim 1 wherein the animal is a human.

3. The process of any one of claims 1 or 2 wherein the compound is threonine.

4. The process of any one of claims 1 or 2 wherein the compound is tyrosine.

5. A composition comprising a mixture of (a) a compound selected from the group consisting of tyrosine, phenylalanine, threonine or mixtures thereof and (b) a drug selected from the group consisting of procaine amide, quinidine, propranolol, disopyramide or pharmaceutically acceptable salts thereof and mixtures thereof in an amount effective to prevent or treat ventricular fibrillation wherein the dosage of (a) is between about 0.5 and about 20 mg/kg body weight.

6. The composition of claim 5 wherein the compound is tyrosine.

7. The composition of claim 5 wherein the compound is threonine.

* * * * *